United States Patent [19]

Bretting

[11] Patent Number: 5,447,924
[45] Date of Patent: Sep. 5, 1995

[54] VITAMIN D ANALOGUES

[75] Inventor: Claus Aage S. Bretting, Frederiksberg, Denmark

[73] Assignee: Leo Pharmaceutical Products Ltd., Ballerup, Denmark

[21] Appl. No.: 927,420

[22] Filed: Sep. 22, 1992

[30] Foreign Application Priority Data

Aug. 15, 1990 [GB] United Kingdom ............... 9017890

[51] Int. Cl.6 ........................................... A61K 31/59
[52] U.S. Cl. ..................................... 514/167; 552/653
[58] Field of Search ........................... 552/653; 514/167

[56] References Cited

U.S. PATENT DOCUMENTS

| | | | |
|---|---|---|---|
| 4,594,432 | 6/1986 | Baggiolini et al. | 514/167 |
| 4,612,308 | 9/1986 | Baggiolini et al. | 514/167 |
| 4,617,279 | 10/1986 | Manake et al. | 514/167 |
| 4,711,881 | 12/1987 | Ikekawa | 514/167 |
| 4,719,205 | 1/1988 | DeLuca et al. | 514/167 |
| 4,804,502 | 2/1989 | Baggiolini et al. | 514/167 |
| 4,832,875 | 5/1989 | Ikekawa | 514/167 |
| 4,851,401 | 7/1989 | DeLuca et al. | 514/167 |
| 4,868,165 | 9/1989 | Ikekawa | 514/167 |
| 5,190,935 | 3/1993 | Binderup et al. | 514/167 |
| 5,194,431 | 3/1993 | DeLuca et al. | 514/167 |
| 5,200,536 | 4/1993 | Ikekawa et al. | 514/167 |
| 5,260,290 | 11/1993 | DeLuca et al. | 514/167 |
| 5,292,728 | 3/1994 | Neef et al. | 514/167 |

FOREIGN PATENT DOCUMENTS

| | | |
|---|---|---|
| 326875 | 8/1989 | European Pat. Off. |
| 398217 | 11/1990 | European Pat. Off. |
| 91/00271 | 1/1991 | WIPO |
| 91/00855 | 1/1991 | WIPO |

Primary Examiner—Johann Richter
Assistant Examiner—Kimberly J. Kestler
Attorney, Agent, or Firm—Cushman Darby & Cushman

[57] ABSTRACT

Vitamin D analogues of the formula:

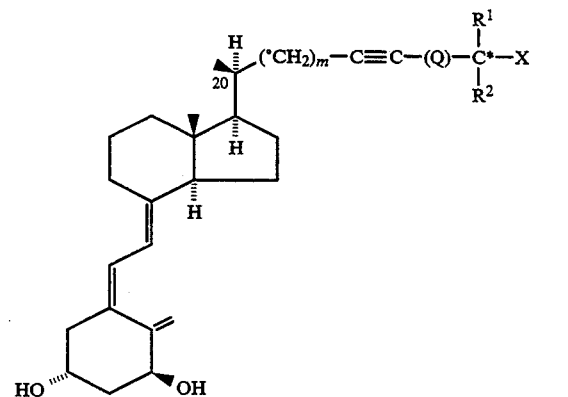

wherein X is hydrogen or hydroxy; $R^1$ and $R^2$ are each hydrogen or $C_1$-$C_6$ hydrocarbyl or $R^1$ and $R^2$ together with the starred carbon form a $C_3$-$C_8$ carbocyclic ring; Q is a single bond or a $C_1$-$C_8$ hydrocarbylene diradical; and m is 0, 1 or 2. One of the m carbons designated by ° may be optionally substituted with deuterium, fluorine or $C_1$-$C_2$ alkyl. $R^1$, $R^2$ and/or Q may also be substituted with deuterium or fluorine. The analogues show, for example, anti-inflammatory and immunomodulating effects.

6 Claims, No Drawings

VITAMIN D ANALOGUES

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, for promoting osteogenesis and treating osteoporosis, and a number of disease states including diabetes mellitus, hypertension, ache, alopecia, skin ageing, imbalance in the immune system, inflammatory diseases such as rheumatoid arthritis and asthma as well as diseases characterized by abnormal cell differentiation and/or cell proliferation such as e.g. psoriasis and cancer.

The compounds of the invention constitute a novel class of vitamin D analogues and are represented by the general formula I

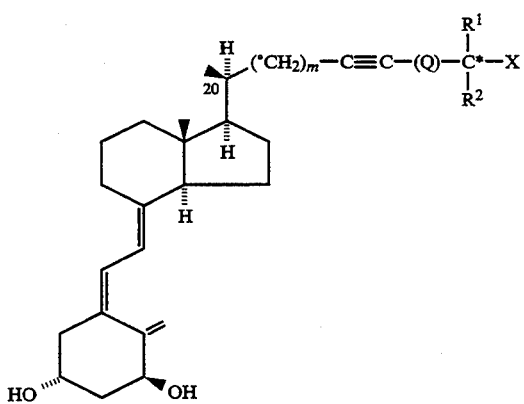

in which formula X is hydrogen Or hydroxy; $R^1$ and $R^2$, which may be the same or different, stand for hydrogen or $C_1$-$C_6$ hydrocarbyl; or $R^1$ and $R^2$ taken together with the carbon atom (starred in formula I) bearing the group X, can form a $C_3$-$C_8$ carbocyclic ring; Q is a single bond or a $C_1$-$C_8$ hydrocarbylene diradical. m is 0, 1 or 2. $R^1$, $R^2$ and/or Q may be optionally substituted with one or more deuterium or fluorine atoms.

In addition, one of the m carbons designated by the "*" may be optionally substituted with one or more deuterium or fluorine atom(s), or one or two $C_1$-$C_2$ alkyl group(s).

In the context of this invention, the expression hydrocarbyl radical (hydrocarbylene diradical) indicates the residue after removal of 1 (2) hydrogen atom(s) from a straight, branched or cyclic saturated or unsaturated hydrocarbon.

Examples of $R^1$ and $R^2$ when taken separately include (apart from hydrogen), but are not limited to, methyl, trifluoromethyl, ethyl, vinyl, normal-, iso- and cyclopropyl, and 1-methylvinyl.

Examples of $R^1$ and $R^2$ when taken together include di-, tri-, tetra- and penta-methylene.

Examples of Q include a single bond, methylene, di-, tri- and tetra-methylene, —$CH_2$—CH=CH—, —$CH_2$—C≡C—, phenylene ($C_6H_4$; ortho, meta, para), —$CH_2$—($C_6H_4$)—, and —($C_6H_4$)—$CH_2$.

As can be seen from formula I, depending on the meanings of $R^1$, $R^2$, Q and X the compounds of the invention can comprise several diastereoisomeric forms (e.g. R or S configuration at the starred carbon atom). The invention covers all these diastereoisomers in pure form and also mixtures of diastereoisomers. In addition, derivatives of I in which one or more of the hydroxy groups are masked as groups which can be reconverted to hydroxy groups in vivo are also within the scope of the invention ("bioreversible derivatives or prodrugs of I").

The term "bioreversible derivatives or prodrugs of I" includes, but is not limited to, derivatives of the compounds of formula I in which one or more hydroxy groups have been transformed into —O-acyl or —O-glycosyl or phosphate ester groups, such masked groups being hydrolyzable in vivo.

Compounds of formula I in which X is hydrogen also may act as prodrugs, as these compounds are relatively inactive in vitro, but are converted to active compounds of formula I by enzymatic hydroxylation after administration to the patient.

It has recently been shown that 1α,25-dihydroxyvitamin $D_3$ (1,25(OH)$_2$$D_3$) influences the effects and/or production of interleukins (Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25(OH)$_2$$D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25(OH)$_2$$D_3$, or its pro-drug 1α—OH—$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for 1,25(OH)$_2$$D_3$ is suggested by the recent observation of an association between hereditary vitamin D resistance and alopecia: treatment with 1,25(OH)$_2$$D_3$ may promote hair growth (Lancet, Mar. 4, 1989, p. 478). Also, the fact that topical application of 1,25(OH)$_2$$D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of 1,25(OH)$_2$$D_3$ are severely-limited by the well known potent effect of this hormone on calcium metabolism; elevated blood concentrations will rapidly give rise to hyercalcemia. Thus, this compound and its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, MC 903, containing a 22,23-double bond, a 24-hydroxy group and in which the carbon atoms 25, 26 and 27 are incorporated in a three membered ring, is a potent inducer of cell differentiation and inhibitor of cell proliferation which shows only moderate activity on calcium metabolism in vivo (Binderup, L. and Bramm, E., Biochemical Pharmacology 37, 889–895 (1988)). However, this selectivity is not paralleled by in vitro studies, which show that MC 903 binds equally well as $1,25(OH)_2D_3$ to the intestinal vitamin D receptor. It may therefore be that the low in vivo activity on calcium metabolism of MC 903 is due to a rapid metabolism of the compound, thus limiting the potential of this compound for systemic use.

24-Homo-1,25-dihydroxyvitamin $D_3$ and 26-homo-1,25-dihydroxyvitamin $D_3$ (together with their 22,23-didehydroanalogues) (Ostrem, V. K.; Tanaka, Y.; Prahl, J.; DeLuca, H. F.; and Ikekawa, N.; Proc. Natl. Acad. Sci. USA 84, 2610–14 (1987)) have been claimed to have the same binding affinity as $1,25(OH)_2D_3$ to both the rat and chicken intestinal receptor and the receptor in a human myeloid leukemia cell line (HL-60), and yet to be 10-fold more potent than $1,25(OH)_2D_3$ in inducing differentiation of HL-60 cells in vitro. In vivo, these compounds are respectively "significantly less potent" and "more potent" than $1,25(OH)_2D_3$ in calcium metabolism assessments.

26,27-Dimethyl-$1\alpha$,25-dihydroxyvitamin $D_3$ has been synthesized, but the published information regarding its biological acitivities is contradictory. (Sai, H.; Takatsuto, S.; Hara, N.; and Ikekawa, N.; Chem. Pharm. Bull. 33, 878–881 (1985) and Ikekawa, N.; Eguchi, T.; Hara, N.; Takatsuto, S.; Honda, A.; Mori, Y.; and Otomo, S.; Chem. Pharm. Bull. 35, 4362–4365 (1987)). The closely related 26,27-diethyl-$1\alpha$,25-dihydroxyvitamin $D_3$ is also reported by these authors; in this case as having "almost no vitamin D activity" (i.e. calcium metabolism effects) while being 10-fold more potent than $1,25(OH)_2D_3$ in inducing cell differentiation.

U.S. Pat. No. 4,804,502 discloses compounds containing a triple bond in the side chain of Vitamin D, and these compounds are claimed to be useful in the treatment of disease states characterized by metabolic calcium deficiencies.

The fact that there are only small structural differences between the above compounds indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

The compounds of the present invention differ structurally from the above vitamin D analogues, some of which have been reported to have potent effects on cell differentiation/proliferation in the configuration of the methyl group at carbon-20. This "unnatural" configuration present in the compounds I (and also in compounds according to our previous international patent application PCT/DK90/00156, filing date 19th Jun., 1990, publication number WO 91/00271) has surprisingly been found to have a profound and advantageous biological significance. Thus a particular compound of formula I, when compared to the corresponding compound containing the "natural" C-20 configuration (methyl and hydrogen radicals exchanged), is observed to show one or more of the following advantages:

(a) more potent effects on cell differentiation/proliferation;

(b) a greater selectivity in favour of the potent effects on cell differentiation/proliferation contra the effects on calcium metabolism;

(c) more potent effects on the production and action of interleukins;

(d) a greater selectivity in favour of the effects on interleukin production and action contra the effects on calcium metabolism.

The compounds of the invention are therefore especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g in autoimmune diseases, including diabetes mellitus, host versus graft reaction, and rejection of transplants; and additionally for the treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin ageing, including photo-ageing.

Because of the low tendency of the compounds to produce hypercalcemia on continued administration they are expected to be valuable for the long term treatment of hyperparathyroidism (particularly secondary hyperparathyroiddism associated with renal failure) and for promoting osteogenesis and treating osteoporosis. For these indications the presently described compounds have a higher therapeutic ratio than the prior art compounds (see U.S. Pat. No. 4,948,789 and EP 0385446 A2).

The present compounds may be used in combination with other pharmaceuticals. In the prevention of graft rejection and graft versus host reaction, a treatment with the present compounds may advantageously be combined with e.g. a cyclosporin treatment.

Compounds I can be prepared from the vitamin D-derived aldehyde II (m=0) (Scheme 1); a synthesis of which has been reported [M. J. Calverley, Tetrahedron 43, 4609 (1987)], for example by the routes outlined in Scheme 1–4. For m=0, the aldehyde II (m=0) is the starting material of Scheme 2; for m=1 or m=2, side chain (20) homologated aldehydes of formula II are used instead of II (m=0). For m=1, the 20-homo-, for m=2, the 20-bis-homo-analogues, II, are the starting materials of Scheme 2. While such 20-homo or 20-hishomo compounds II may be synthesized in many different ways, known to the specialist, suitable standard reactions, e.g. as described in: R. C. Larock, "Comprehensive Organic Transformations", VCH 1989, 733, are preferred. If necessary, a temporary protection of the sensitive triene system of the molecule may be involved.

The conversion of compounds II into the compounds III and IV of Scheme 2 may conveniently be performed by a two-step method which is well known for transforming an aldehyde into an alkyne, and have been used in e.g. steroid chemistry (see for example Burger, A. et al, Tetrahedron 44, 1141 (1988)), but which has not before been applied to vitamin-D chemistry. The method comprises a Wittig-type conversion of aldehyde II into the dihalovinyl derivative III, followed by an elimination-alkylation reaction under anhydrous, basic conditions (butyllithium in tetrahydrofuran (THF)) preferably with a catalyst e.g. hexamethylphosphoramide (HMPA) added, in order to accelerate the reaction. The alkylation of the, not isolated, intermediate-anion —C≡C⊖ (i.e. the lithium acetylide, LA) derived from III to give IV is achieved by treatment with a side chain building block of general formula Z—R, in which Z is a leaving group such as a halogen (Cl, Br or I) or p-toluenesulphonyloxy, methanesulphonyloxy, or trifluoromethanesulfonyloxy, and R is —(Q-)—C(R$^1$)(R$^2$)X or optionally a radical which can be converted to this at any convenient later stage (or over several stages). Thus R in compounds IV, V and VI does not necessarily have the same meaning along a particular synthetic sequence. The conversion of R to —(Q)—C(R$^1$)(R$^2$)X may well involve several steps and possibly involve a temporary protection of the sensitive triene system of the molecule. Apart from any necessary modification within the side chain (R), the conversion of IV to I involves a photoisomerisation step and a desilylation step, analogous to the steps used in the last stages of the synthesis of other vitamin D analogues (see European patent No. 0 227 826).

In the special cases where Q is a single bond or Q=CH$_2$, IV may conveniently be prepared by the cognate procedures depicted in Scheme 3, which illustrate the transformation of the nucleophilic LA into compounds IV, by other electrophiles than RZ; that is, by aldehydes and ketones, by oxiranes, and the double transformation by methyl iodide, followed by butyllithium and then an aldehyde or ketone.

Similarly, in the special cases where Q=(CH$_2$)$_2$, IV may sometimes be prepared advantageously by one of the cognate procedures depicted in Scheme 4, which also illustrate both the subsequent conversion of the radical R, after the alkylation of LA by RZ, into the desired R of compound IV, and the reaction of LA with oxetanes; and aditionally the reaction of LA with MeI, then BuLi, and finally an oxirane.

It may be convenient to change the order of the alkylation reaction and the photoisomerisation reaction (d), in which case the (5Z)-isomer of III is a key intermediate.

The side chain building blocks, RZ, are either known compounds (several are described in international patent application pCT/DK89/00079) or may be prepared analogously to those described in PCT/DK89/00079. The R is typically —(Q)—C(R$^1$)(R$^2$)X$^1$ in which X$^1$ is hydrogen or an OH group or a protected OH group, e.g. tetrahydropyranyloxy or trialkylsilyloxy. (Any such THP ethers RZ, which are not described in PCT/DK89/00079, are readily prepared from the corresponding alcohol).

The following standard abbreviations are used throughout this disclosure: Me=methyl; Et=ethyl; Pr$^n$=n-propyl; Pr$^i$=isopropyl; Bu=n-butyl; Bu$^t$=tert-butyl; THP=tetrahydro-4H-pyran-2-yl; HMPA=hexamethylphosphoramide; THF=tetrahydrofuran; Ts=p-toluenesulphonyl; TBA=tetra-(n-butyl)-ammonium; DMF=dimethylformamide.

In Schemes 1–4, the following abbreviation is used:

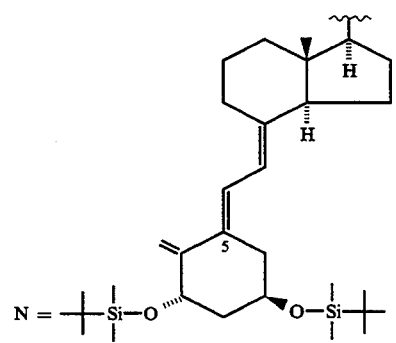

In the Notes to Schemes 1–4, appropriate aqueous work-up steps are implicit.

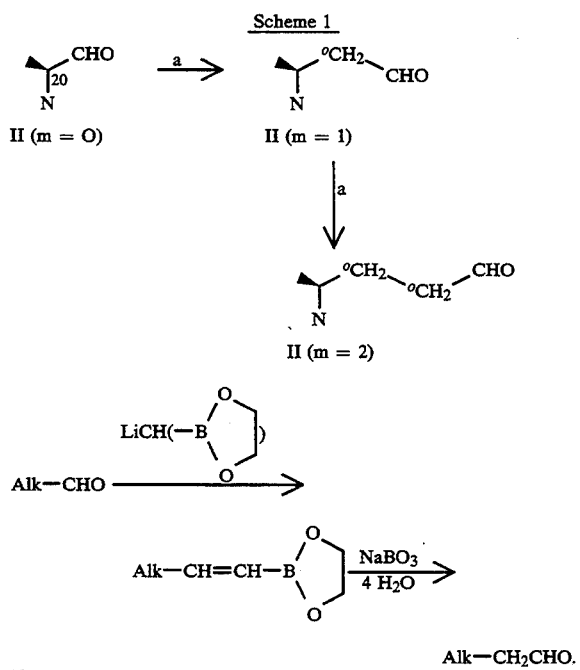

Notes to Scheme 1
a An especially preferred reaction, which avoids acidic conditions, is (Matteson, D.S. and Moody, R.J., J. Org. Chem. 45 (1980) 1091):

Other preferred procedures are e.g.:

1) A sequence of reactions, which are analogous to the ones described in the literature for the synthesis of the corresponding 20(S) ("20-normal") 20-homoaldehydes (Calverley, M. J., Tetrahedron Left, 28, 1337 (1987) and Calverley, M. J., Synlett, 155 (1990)):

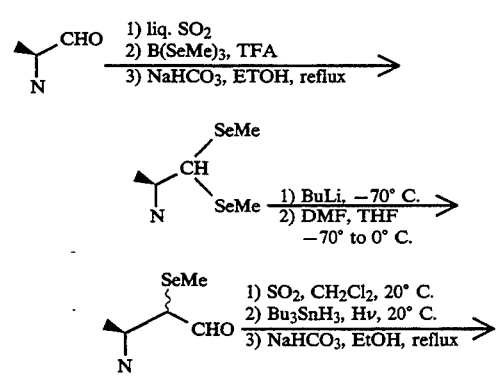

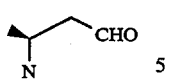

2) A method analogous to a described synthesis (Wowkulich et al., Tetrahedron, 40, 2283 (1984)) in the C,D ring series:

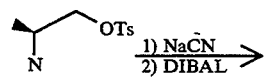

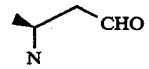

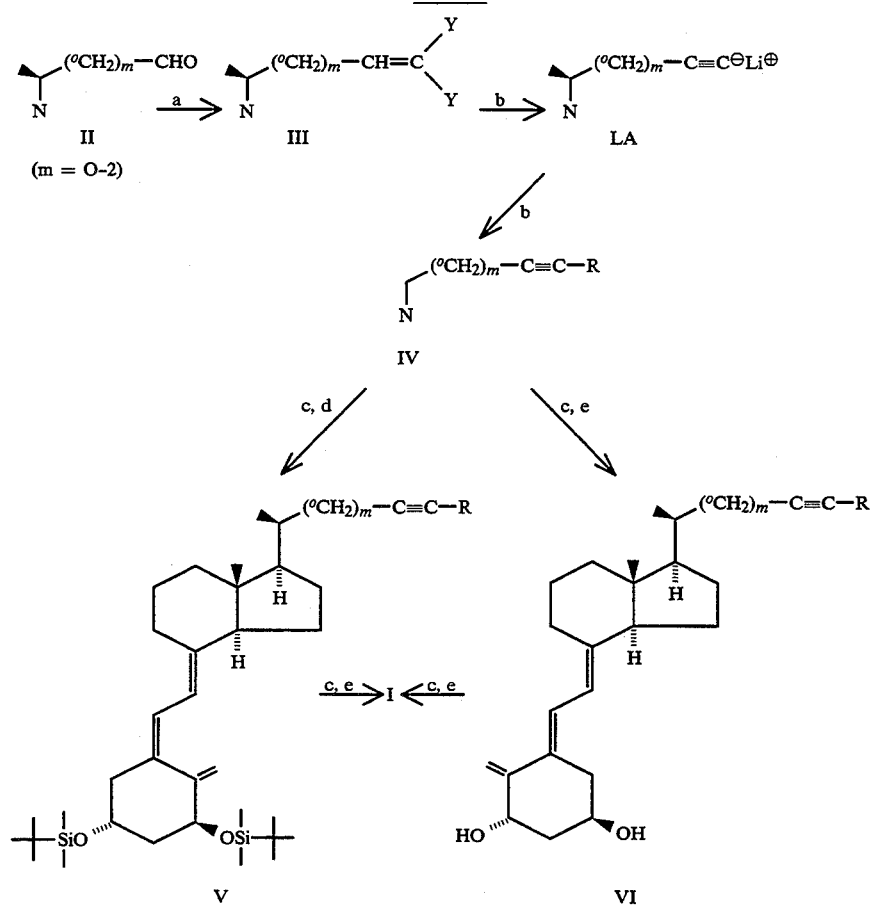

Notes to Scheme 2 a Reaction with a Wittig-type reagent, e.g. [(CH$_3$)$_2$N]$_3$P=CCl$_2$ or (C$_6$H$_5$)$_3$P=CBr$_2$ (see for example Salmond, W.G. et al., Tetrahedron Letters, 1977, 1141), (Y = Cl, resp. Br), in a suitable anhydrous solvent (e.g. dichloromethane).

b Treatment of III with two moles of a base, e.g. BuLi, to give the intermediate lithium acetylide, LA, followed by alkylation with the side chain building block R-Z with or without catalyst (e.g. HMPA) in an anhydrous solvent (e.g. THF).

c Optional functional group modification in the side chain.

d Isomerisation with hv-triplet sensitizer, e.g. anthracene.

e Deprotection with TBA$^+$F$^-$ or HF.

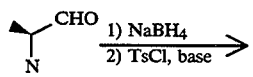

It should be noted that although the shown intermediates may have hydroxyl groups protected as tert-butyldimethylsilyl ethers, the scope of the invention does not exclude the use of alternative hydroxyl protecting groups well known in the art (such as those described in T. W. Greene, "Protective groups in organic synthesis", Wiley, New York, 1981), together with alternative reactions for deprotection.

Scheme 3
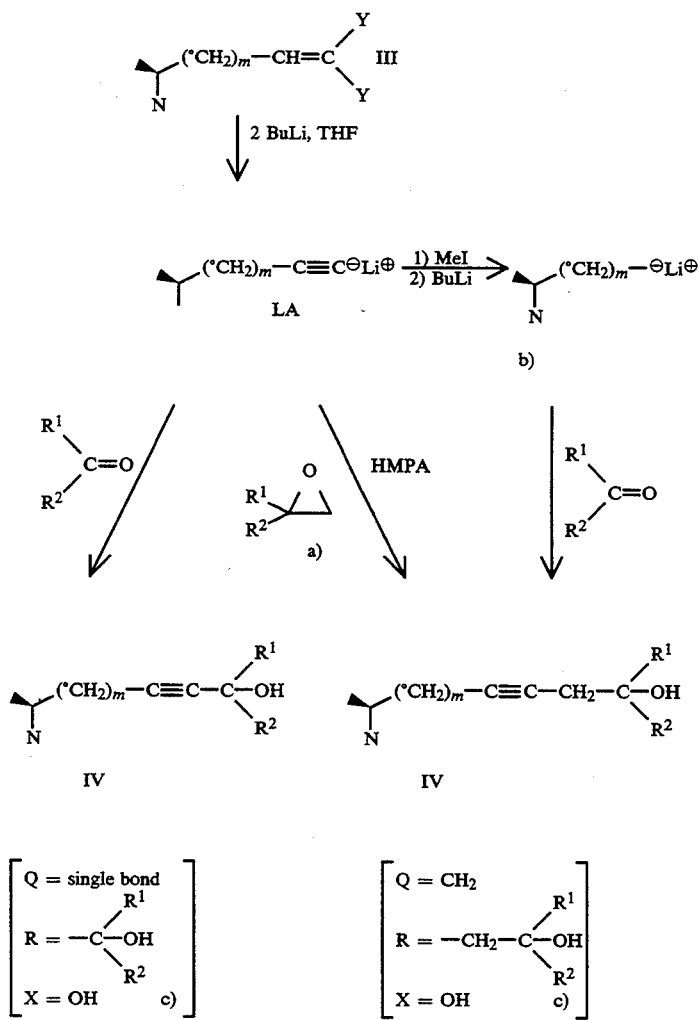
Scheme 4
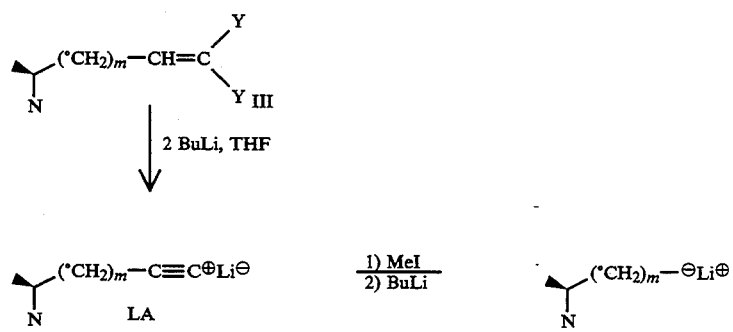

-continued

Scheme 4

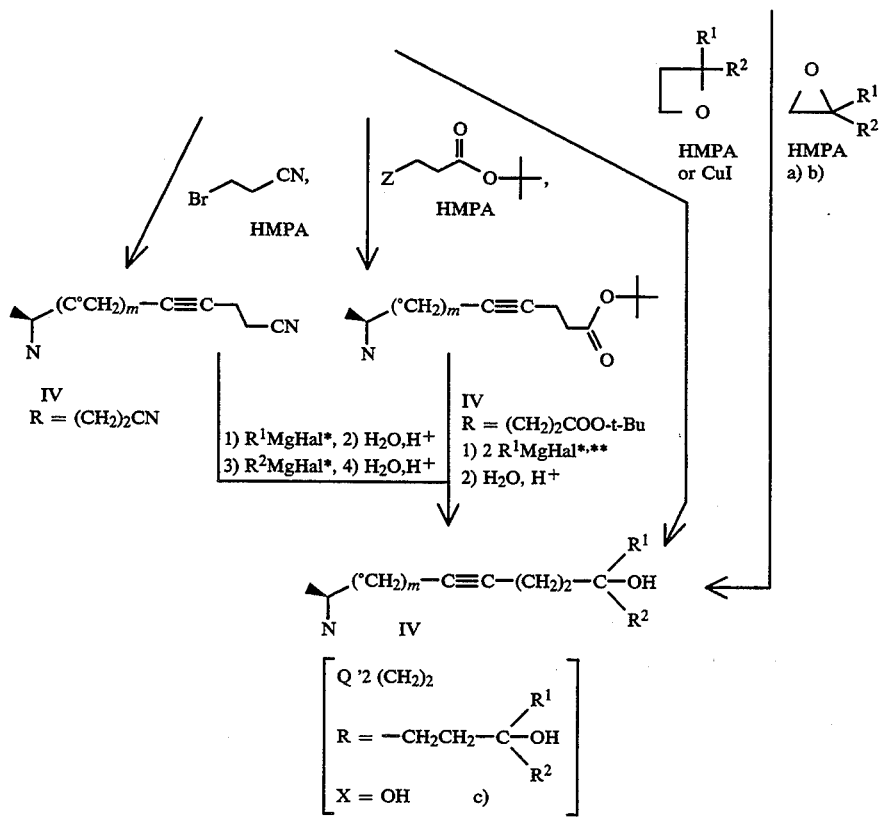

*Hal = Cl, Br, I
**R¹ = R²

Notes to Schemes 3 and 4 a) See e.g. Salmond, W.G. et al., Tetrahedron Letters, 1977, 1237.

b) See e.g. Burger, A. et al, Tetrahedron 44 (1988) 1141.

c) The compounds IV or Schemes 3 and 4 have thus an unprotected hydroxyl group in the side chain fragment, R. The further steps from IV to I, via V or VI, are the same as outlined in Scheme 2.

In addition to the preparations of Compounds I by the methods depicted in Schemes 2, 3 and 4, other methods known from the literature may also, by analogy, be used. There may, however, depending on the nature of $(^\circ CH_2)_m$, Q, $R^1$, $R^2$ and $X^1$, be limitations as to the applicability of such methods in each special case. A temporary protection of the sensitive triene-system, e.g. by means of liq. $SO_2$, may in some cases be necessary. Some such methods for the preparation of the intermediate IV (of Schemes 2, 3 and 4) are illustrated in Scheme 5 and Scheme 6:

Scheme 5

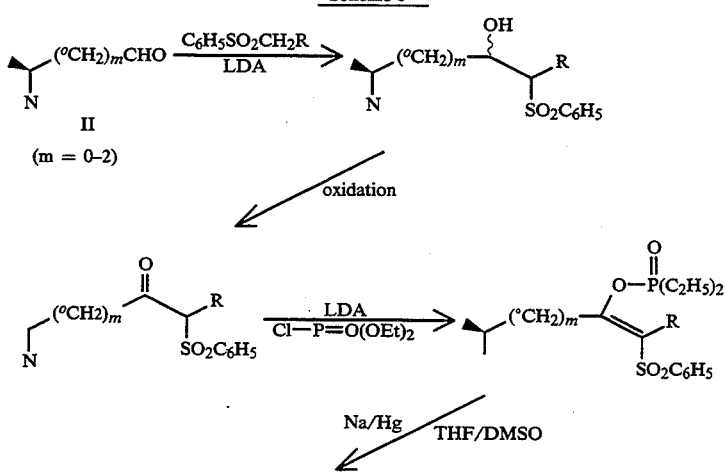

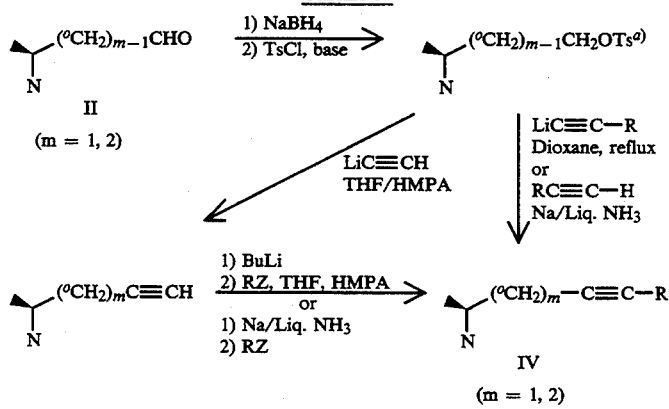

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined Mount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100µ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and fluorinated $C_1$-$C_6$-alkyl hydrocarbons are especially preferred. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1-100 µg, preferably from 0.2-25 µg, of a compound of formula I are administered. In the topical treatment of dermatological disorders, ointments, creams or lotions containing from 0.1-500 µg/g, and preferably from 0.1-100 µg/g, of a compound of formula I are administered. For topical use in ophthalmology ointments, drops or gels containing from 0.1-500 µg/g, and preferably from 0.1-100 µg/g, of a compound of formula I are administered. The oral compositions are formulated, preferably as tablets, capsules, or drops, containing from 0.05-50 µg, preferably from 0.1-25 µg, of a compound of formula I, per dosage unit.

The invention will now be further described in the following non-limiting Preparations and Examples:

PREPARATION AND EXAMPLES

General

The exemplified compounds I are listed in Table 1.

For nuclear magnetic resonance spectra (300 MHz) chemical shift values ($\delta$) are quoted for deuteriochloroform solutions relative to internal tetramethylsilane ($\delta = 0$) or chloroform ($\delta = 7.25$). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

PREPARATION 1

1(S),3(R)-bis-tert-butyldimethylsilyloxy-20(R)-2,2-dichlorovinyl-9,10-seco-pregna-5(E),7(E),10(19)-triene
(Compound 1)

To a solution of the aldehyde II (m=0) (1.15 g) and bromotrichloromethane (0.44 g) in dry dichloromethane (6 ml), cooled to −20° C. and stirred under argon, was added dropwise, during 40 minutes, a solution of tris(dimethylamino)phosphine (0.72 g) in dry dichloromethane (4 ml). The mixture was stirred for another 30 minutes at −20° C. and then for 20 hours at 20° C. The mixture was partitioned between dilute brine (75 ml) and dichloromethane (75 ml), and the organic layer was washed with water and dried. Concentration in vacuo gave a residue which was purified by chromatography (1% ether in petroleum ether as eluant), and followed by crystallisation from methanol to yield the title compound.

M.p. 120°-123° C.

NMR: $\delta = 0.06$ (m, 12H), 0.51 (s, 3H), 0.86 (s, 9H), 0.89 (s, 9H), 0.96 (d, 3H), 1.00–2.10 (m, 13H), 2.30 (bd, 1H), 2.43 (m, 1H), 2.55 (dd, 1H), 2.88 (dd, 1H), 4.21 (m, 1H), 4.53 (m, 1H), 4.94 (m, 1H), 4.98 (m, 1H), 5.71 (d, 1H), 5.82 (d, 1H), 6.45 (d, 1H).

PREPARATION 2

1(S),3(R)-bis-tert-butyldimethylsilyloxy-20(R)-(6'-ethyl-6'-trimethylsilyloxy-oct-1'-yn-1'-yl)-9,10-secopregna-5(E),7(E),10(19)-triene (Compound 2)

To a solution of Compound 1 (0.28 g) in dry THF (16 ml), cooled to −70° C. and stirred under argon, was added dropwise, during 5 minutes a solution of butyllithium (1.6M in hexane, 0.7 ml). Stirring was continued at −70° C. for one hour and then at 20° C. for two hours. The mixture was cooled to −10° C. and 1-bromo-4-ethyl-4-trimethylsilyloxyhexane (0.38 g) was added, during 3 minutes, followed by dry HMPA (2 ml), during 4 minutes. Stirring was continued at −10° C. for 7 minutes and then at 20° C. for three hours. The reaction mixture was poured into 25 ml half-saturated brine and extracted with ether (2×50 ml). The combined organic phase was extracted (quickly) with 1N hydrochloric acid (25 ml), with 1% aqueous sodium bicarbonate (25 ml), with water (25 ml) and with brine (25 ml). After drying with $MgSO_4$ and concentration in vacuo, an oil was obtained which was purified twice by chromatography (first with 2% ether in petroleum ether, next with 0.2% ethyl acetate in hexane as eluants) to yield the title compound.

NMR: $\delta$=0.05 (m, 12H), 0.09 (s, 9H), 0.57 (s, 3H), 0.81 (t, 6H), 0.85 (s, 9H), 0.89 (s, 9H), 1.11 (d, 3H), 1.45 (q, 4H), 1.00–2.08 (m, 16H), 2.12 (m, 2H), 2.22 (m, 1H), 2.31 (bd, 1H), 2.41 (bd, 1H), 2.55 (dd, 1H), 2.88 (bd, 1H), 4,21 (bd, 1H), 4.53 (m, 1H), 4.93 (m, 1H), 4.98 (m, 1H), 5.81 (d, 1H), 6.46 (d, 1H).

PREPARATION 3

1(S),3(R)-bis-tert-butyldimethylsilyloxy-20(R)-(6'-ethyl-6'-trimethylsilyloxy-oct-1'-yn-1'-yl)-9,10-secopregna-5(Z),7(E),10(19)-triene (Compound 3)

A solution of Compound 2 (20 mg), anthracene (10 mg) and triethylamine (0.005 ml) in dichloromethane (4 ml) under argon in a Pyrex flask was irradiated with light from a high pressure ultraviolet lamp, type TQ 760Z2 (Hanau) at about 10° C. for 20 minutes under stirring. The reaction mixture was concentrated in vacuo and treated with petroleum ether (1 ml) containing 0.25% triethylamine. After filtrering, the filtrate was concentrated in vacuo and purified by chromatography (1% ether in petroleum ether as eluant) to yield the title compound.

NMR: $\delta$=0.05 (m, 12H), 0.09 (s, 9H), 0.56 (s, 3H), 0.81 (t, 6H), 0.86 (s, 9H), 0.87(s, 9H), 1.11 (d, 3H), 1.44 (q, 4H), 0.85–2.75 (m, 22H), 2.83 (bd, 1H), 4.18 (m, 1H), 4.36 (m, 1H), 4.85 (m 1H), 5.17 (m, 1H), 6.00 (d, 1H), 6.24 (d, 1H).

PREPARATION 4

1(S),3(R)-bis-tert-butyldimethylsilyloxy-20(R)-(7'-ethyl-7'-trimethylsilyloxy-non-1'-yn-1'-yl)-9,10secopregna-5(E),7(E),10(19)-triene (Compound 4)

By following the procedure of preparation 2, but substituting 1-bromo-5-ethyl-5-trimethylsilyloxyheptane for 1-bromo-4-ethyl-4-trimethylsilyloxyhexane, the title compound was obtained.

NMR: $\delta$=0.05 (m, 12H), 0.09 (s, 9H), 0.57 (s, 3H), 0.80 (t, 6H), 0.86 (s, 9H), 0.89 (s, 9H), 1.11 (d, 3H), 1.15–2.5 (m, 23H), 1.43 (q, 4H), 2,55 (m, 1H), 2.88 (m, 1H), 4,22 (m, 1H), 4.53 (m, 1H), 4.93 (m, 1H), 4.98 (m, 1H), 5.81 (d, 1H), 6.46 (d, 1H).

PREPARATION 5

1(S),3(R)-bis-tert-butyldimethylsilyloxy-20(R)-(7'-ethyl-7'-trimethylsilyloxy-non-1'-yn-1'-yl)-9,10-secopregna-5(Z),7(E),10(19)-triene (Compound 5)

By following the procedure of preparation 3, but substituting Compound 4 for Compound 2, the title compound was obtained.

NMR: $\delta$=0.05 (m, 12H), 0.10 (s, 9H), 0.56 (s, 3H), 0.80 (t, 6H), 0.86 (s, 18H), 1.10 (d, 3H), 1.05–1.93 (m, 22H), 1.98 (bt, 1H), 2.15 (m, 2H), 2.21 (dd, 1H), 2.38 (bd, 1H), 2.44 (dd, 1H), 2.83 (dd, 11{), 4.18 (m, 11{), 4.36 (m, 1H), 4,86 (m, 1H), 5.17 (m, 11{), 6.00 (d, 11{), 6.24 (d, 1H).

GENERAL PROCEDURE 1

Homologation of the Aldehyde II (m=0 or 1) to the Next Higher Homologue (Scheme 1)

To a solution of tris(ethylenedioxyboryl)methane (2.6 g) in a mixture of dry THF (10 ml) and dry dichloromethane (10 ml), cooled to −78° C. and stirred under argon, a solution of methyllithium (1.6M in ether; 7.2 ml) is added dropwise and stirring is continued for 2.5 hours at −78° C. The aldehyde II (m=0 or 1) (10 mmoles) is added and the mixture stirred for 3 hours at room temperature. The solvents are removed in vacuo, and 20 ml of water and 20 ml of dichloromethane are added, followed by 2.0 g sodium perborate tetrahydrate at 0° C. The mixture is stirred for 1.5 hours at 20° C. and worked up. Purification by chromatography (10% ether in petroleum ether) yields II (m=1 or m=2).

GENERAL PROCEDURE 2

Preparation of the Dihalovinyl Compounds III of Scheme 2

By using the procedure of Preparation 2,but substituting for Compound II (m=0), the compounds II, where m=1 or m=2, the corresponding Compounds III of Scheme 2 are prepared.

GENERAL PROCEDURE 3

Preparation of the Intermediate Lithium Acetylide (LA) of Scheme 2, 3 and 4

Butyllithium in hexane (1.2 mmol) is added dropwise to a stirred solution (-78° C.) of the appropriate Compound III of Scheme 2 (0.56 mmol) in dry THF (20 ml) under argon. Stirring is continued for 1 hour at −78° C. and another 2 hours at room temperature to give the LA of Schemes 2, 3 and 4.

GENERAL PROCEDURE 4

Alkylation of the Intermediate Lithium Acetylide (LA) of General Procedure 2 with the Side Chain Building Block Z—R of Scheme 2

The appropate dry Z—R (1.7 mmol) and dry HMPA (2 ml) are added dropwise to a stirred and cooled solution (−10° C.) of the LA of general procedure 3. After stirring at room temperature until the reaction is complete, the reaction mixture is worked up in the same manner as described in Preparation 2 and purified by chromatography (1–10% ether in petroleum ether), to give the compounds IV of Scheme 2.

GENERAL PROCEDURE 5

Reaction of the Intermediate Lithium Acetylide (LA) of General Procedure 3 with R¹COR² of Scheme 3

The appropriate dry aldehyde or ketone R¹COR² (1 mmole) is added dropwise to a stirred and cooled solution (−10° C.) of the LA of general procedure 3. After stirring at room temperature until the reaction is complete, the reaction mixture is worked up (ether) and purified by chromatography (1–10% ether in petroleum ether), to give the compounds IV of Scheme 3 where Q is a single bond.

GENERAL PROCEDURE 6

Reaction of the Intermediate Lithium Acetylide (LA) of General Procedure 3 with

of Scheme 3 or

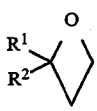

of Scheme 4

By using general procedure 4, but substituting for Z—R the appropriate dry oxirane,

or oxetane

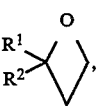

the Compounds IV of Scheme 3 where Q=CH$_2$ or the Compounds IV of Scheme 4 where Q=(CH$_2$)$_2$ are prepared.

GENERAL PROCEDURE 7

Reaction of the Intermediate Lithium Acetylide (LA) of General Procedure 3 with MeI, BuLi and R¹COR² of Scheme 3

MeI (0.05 ml) is added dropwise to a stirred and cooled solution (−10° C.) of the LA of general procedure 3. After stirring for 3 hours at room temperature, the solution is cooled to 0° C., and BuLi in hexane (1.35 mmole) is introduced dropwise. The stirring is continued for 2 hours at 0° C., and then the solution is further cooled to −78° C., and the appropriate dry aldehyde or ketone R¹COR²(2.2 mmole) is added dropwise. The reaction mixture is stirred at −78° C. for 1 hour. After work-up (ether) and purification by chromatography (1–10% ether in petroleum ether), the compounds IV of Scheme 3 where Q=CH$_2$ are prepared.

GENERAL PROCEDURE 8

Reaction of the Intermediate Lithium Acetylide (LA) of General Procedure 3 with MeI, BuLi and

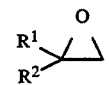

of Scheme 4

By following general procedure 7, but substituting for R¹COR² the appropriate dry oxirane

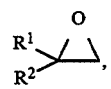

adding dry HMPA (2 ml) and stirring at room temperature until the reaction is complete, the compounds IV of Scheme 4 where Q=(CH$_2$)$_2$ are prepared.

GENERAL PROCEDURE 9

Preparation of Compounds IV of Scheme 4 with Conversion of the R-Radical

The compounds IV of Scheme 4 where R=(CH$_2$)$_2$CN or R=(CH$_2$)$_2$COO-t-Bu (prepared by general procedure 4 using as RZ, Br(CH$_2$)$_2$CN or ZCH$_2$COO-t-Bu) are added to an excess of Grignard reagent R¹MgHal in a suitable solvent (e.g. ether, THF or benzene or a mixture thereof) and stirring for a sufficient time and at a temperature which may be raised to the boiling point of the solvent, the compounds IV of Scheme 4 where R=CH$_2$CH$_2$C(R¹)$_2$OH (when R was (CH$_2$)$_2$COO-t-Bu) are prepared. In the case when R was (CH$_2$)$_2$CN, a second Grignard reaction similar to the above described using R²MgHal, is necessary to convert the intermediary ketone to the compounds IV of Scheme 4 where R=CH$_2$CH$_2$CR¹R²(OH).

GENERAL PROCEDURE 10

Isomerization of Compounds IV of Scheme 2, 3 and 4 to the corresponding Compounds V of Scheme 2

By using the procedure of Preparation 3, but substituting for Compound 2 the appropriate Compound IV of general procedures 4–9, the Compound V is obtained.

GENERAL PROCEDURE 11

Conversion of Compounds V of Scheme 2 to the Corresponding Compounds I by Desilylation with tetra-n-butylammonium Fluoride (Compounds 101–102 and 104–118)

By using the procedure of Example 1, but substituting for Compound 3 the appropriate Compound V of general procedure 10, the title Compound I is obtained.

TABLE 1

| | | | Exemplified Compounds I | | | |
|---|---|---|---|---|---|---|
| Compound Number | Example Number | m* | Q | R¹ | R² | X |
| 101 | | 0 | CH$_2$ | Et | Et | OH |

TABLE 1-continued

Exemplified Compounds I

| Compound Number | Example Number | m* | Q | R¹ | R² | X |
| --- | --- | --- | --- | --- | --- | --- |
| 102 | | 0 | (CH₂)₂ | Et | Et | OH |
| 103 | 1 | 0 | (CH₂)₃ | Et | Et | OH |
| 104 | | 0 | (CH₂)₃ | Me | Me | H |
| 105 | | 0 | (CH₂)₃ | H | H | OH |
| 106 | | 0 | (CH₂CH₂CH₂C(CH₃)₂ | Me | Me | OH |
| 107** | | 0 | CH₂—CH=CH—CH₂ | Me | Me | OH |
| 108 | | 0 | meta-CH₂—C₆H₄ | Me | Me | OH |
| 109 | | 1 | CH₂ | Et | Et | OH |
| 110+ | | 1 | CH₂ | Cyclo-Pr | H | OH |
| 111++ | | 1 | CH₂ | Cyclo-Pr | H | OH |
| 112 | | 1 | CH₂CF₂ | Me | Me | OH |
| 113 | | 1 | CH₂—C≡C— | Me | Me | OH |
| 114 | | 2 | single bond | Et | Et | OH |
| 115 | | 2 | single bond | CF₃ | CF₃ | OH |
| 116 | | 2 | single bond | —(CH₂)₅— | | OH |
| 117 | | 2 | CH₂ | Me | Me | OH |
| 118 | | 2 | (CH₂)₂ | Et | Et | OH |
| 119 | | 0 | CH₂ | Me | Me | OH |
| 120 | | 0 | CH₂ | CF₃ | CF₃ | OH |
| 121 | | 0 | (CH₂)₂ | Me | Me | OH |
| 122 | | 0 | (CH₂)₂ | CF₃ | CF₃ | OH |
| 123 | | 0 | (CH₂)₂ | Et | Et | H |
| 124 | | 0 | (CH₂)₃ | Me | Me | OH |
| 125+ | | 0 | (CH₂)₃ | Me | Et | OH |
| 126++ | | 0 | (CH₂)₃ | Me | Et | OH |
| 127 | | 0 | (CH₂)₃ | CF₃ | CF₃ | OH |
| 128 | | 0 | (CH₂)₃ | CH₂=CH | CH₂=CH | OH |
| 129 | | 0 | (CH₂)₃ | Et | Et | H |
| 130 | | 0 | (CH₂)₄ | Me | Me | OH |
| 131 | 2 | 0 | (CH₂)₄ | Et | Et | OH |
| 132 | | 1 | Single bond | Me | Me | OH |
| 133 | | 1 | Single bond | Et | Et | OH |
| 134 | | 1 | Single bond | CF₃ | CF₃ | OH |
| 135 | | 1 | CH₂ | Me | Me | OH |
| 136 | | 1 | CH₂ | CF₃ | CF₃ | OH |
| 137 | | 1 | (CH₂)₂ | Me | Me | OH |
| 138 | | 1 | (CH₂)₂ | Et | Et | OH |
| 139 | | 1 | (CH₂)₃ | Me | Me | OH |
| 140 | | 1 | (CH₂)₃ | Et | Et | OH |
| 141 | | 2 | Single bond | Me | Me | OH |
| 142 | | 2 | CH₂ | Et | Et | OH |
| 143 | | 2 | (CH₂)₂ | Me | Me | OH |

*°CH₂ stands for CH₂ in Compounds Nos 101–143
**(E) configuration of double bond in Q
+(R) configuration at starred carbon atom
++(S) configuration at starred carbon atom

EXAMPLE 1

1(S),3(R)-Dihydroxy-2.0(R)-(6'-ethyl-6'-hydroxy-oct-1'-yn-1'-yl)-9,10-seco-pregna-5(Z),7(E),10(19)-triene (Compound 103)

A solution of Compound 3 (12 mg) and tetra-n-butylammonium fluoride trihydrate (31 mg) in THF (1.5 ml) was heated at 60° C. under argon and with stirring for one hour. After cooling, the reaction solution was partitioned between ethyl acetate (8 ml) and 2% sodium hydrogen carbonate solution, containing 4% sodium chloride (8 ml). The organic layer was washed with water and brine, dried and concentrated in vacuo. The residue was purified by chromatography with 20% petroleum ether in ethyl acetate as eluant to give compound 103.

UV: $\lambda_{max}$ (EtOH): 264 nm.

NMR: $\delta$=0.58 (S, 3H), 0.87 (t, 6H), 1.12 (d, 3H), 1.46 (q, 4H), 1.10–2.25 (m, 22H), 2.31 (dd, 1H), 2.40 (bd, 1H), 2.60 (dd, 1H), 2.84 (dd, 1H), 4.23 (m, 1H), 4.43 (m, 1H), 5.00 (m, 1H), 5.32 (m, 1H), 6.01 (d, 1H), 6.39 (d, 1H).

EXAMPLE 2

1(S),3(R)-Dihydroxy-20(R)-(7'-ethyl-7'-hydroxy-non-1'-yn-1'-yl)-9,10-seco-pregna-5(Z),7(E),10(19)-triene (Compound 131)

By following the procedure of Example 1, but substituting Compound 5 for Compound 3, compound 131 was obtained.

UV: $\lambda_{max}$ (EtOH): 263 nm.

NMR: $\delta$=0.58 (s, 3H), 0.86 (t, 6H), 1.11 (d, 3H), 1.30–2.10 (m, 25H), 2.17 (m, 3H), 2.32 (dd, 1H), 2.40 (m, 1H), 2.60 (dd, 1H), 2.85 (dd, 1H), 4.23 (m, 1H), 4.43 (m, 1H), 5.00 (m, 1H), 5.32 (m, 1H), 6.01 (d, 1H), 6.38 (d, 1H).

EXAMPLE 3

Capsules containing Compound 103

103 was dissolved in arachis oil to a final concentration of 1 µg 103/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100

µl of the 103 in oil solution, such that each capsule contained 0.1 µg 103.

EXAMPLE 4

Dermatological Cream Containing Compound 103

In 1 g almond oil was dissolved 0.05 mg 103. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of 103 per gram of cream.

What I claim is:

1. A compound of the formula I

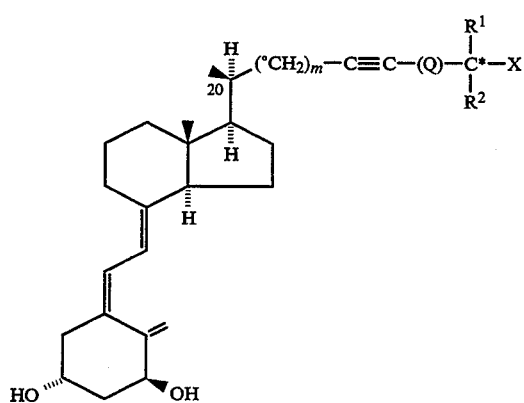

in which formula X is hydrogen or hydroxy; $R^1$ and $R^2$, which may be the same or different, stand for hydrogen or $C_1$–$C_6$ hydrocarbyl; or $R^1$ and $R^2$ taken together with the carbon atom starred in formula I bearing the group X, can form a $C_3$–$C_8$ carbocyclic ring; Q is a single bond or a $C_1$–$C_8$ hydrocarbylene diradical, the expression hydrocarbyl radical or hydrocarbylene diradical indicating the residue after removal of 1 or 2 hydrogen atoms from a straight, branched or cyclic saturated or unsaturated hydrocarbon; m is 0, 1 or 2; $R^1$, $R^2$ and/or Q may be optionally substituted with one or more deuterium or fluorine atoms; in addition, one of the m carbons designated by the "°" may be optionally substituted with one or more deuterium or fluorine atoms, or one or two $C_1$–$C_2$ alkyl groups; or derivatives of the compounds of formula I in which one or more hydroxy groups have been transformed into —O-acyl or —O-glycosyl groups, or a phosphate ester, such masked groups being hydrolyzable in vivo.

2. A diastereoisomer of a compound according to claim 1, in pure form; or a mixture of diastereoisomers of a compound according to claim 1.

3. A compound according to claim 1 which is
   a) 1(S),3(R)-dihydroxy-20(R)-(6'-ethyl-6'-hydroxy-oct-1'-yn-1'-yl)-9,10-seco-pregna-5(Z),7(E),10(19)-triene or
   b) 1(S),3(R)-Dihydroxy-20(R)-(7'-ethyl-7'-hydroxy-non-1'-yn-1'-yl)-9,10-seco-pregna-5(Z),7(E),10(19)-triene.

4. A pharmaceutical composition containing an effective amount of one or more of the compounds of claim 1, together with pharmaceutically acceptable, non-toxic carriers and/or auxiliary agents.

5. A pharmaceutical composition according to claim 4 in dosage unit form.

6. A dosage unit according to claim 5 containing from 0.1 ppm to 0.1% by weight of the dosage unit of a compound of formula I.

* * * * *

UNITED STATES PATENT AND TRADEMARK OFFICE
CERTIFICATE OF CORRECTION

PATENT NO.    :    5,447,924

DATED         :    September 5, 1995

INVENTOR(S)   :    BRETTING

It is certified that error appears in the above-identified patent and that said Letters Patent is hereby corrected as shown below:

Column 1, line 16, change "ache" to --acne--;

Column 1, line 42, change "Or" to --or--;

Column 2, line 61, change "hyercalcemia" to --hypercalcemia--;

Column 5, line 10, change "—C=C$^\ominus$" to -- —C≡C$^\ominus$ --;

Column 5, line 53, change "pCT" to -- PCT --;

Column 6, lines 35-47, change "

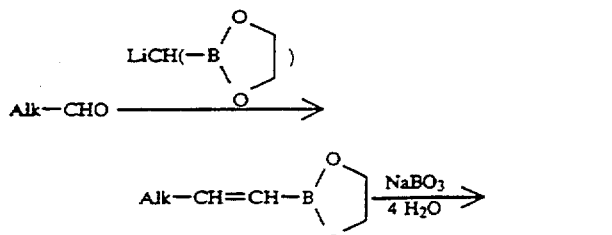

Alk—CH$_2$CHO. "

Notes to Scheme 1
a An especially preferred reaction, which avoids acidic conditions, is (Matteson, D.S. and Moody, R.J., J. Org. Chem. 45 (1980) 1091):

UNITED STATES PATENT AND TRADEMARK OFFICE
CERTIFICATE OF CORRECTION

PATENT NO. : 5,447,924                    Page 2 of 9

DATED     : September 5, 1995

INVENTOR(S) : BRETTING

It is certified that error appears in the above-identified patent and that said Letters Patent is hereby corrected as shown below:

to

--
Notes to Scheme 1
a An especially preferred reaction, which avoids acidic conditions, is (Matteson. D.S. and Moody, R.J., J. Org. Chem. 45 (1980) 1091):

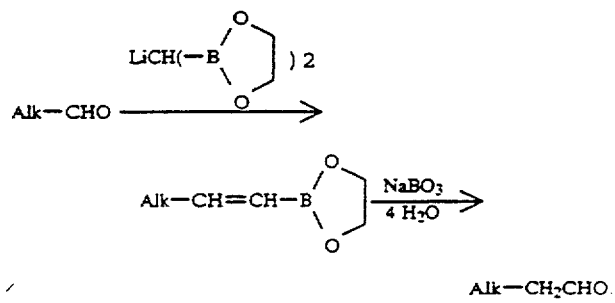

--

Column 6, line 52, change "Left" to -- Lett --;

UNITED STATES PATENT AND TRADEMARK OFFICE
CERTIFICATE OF CORRECTION

PATENT NO.  :     5,447,924          Page 3 of 9

DATED       :     September 5, 1995

INVENTOR(S) :     BRETTING

It is certified that error appears in the above-identified patent and that said Letters Patent is hereby corrected as shown below:

Column 7-8, under "<u>Scheme 2</u>", change

UNITED STATES PATENT AND TRADEMARK OFFICE
CERTIFICATE OF CORRECTION

PATENT NO. : 5,447,924　　　　　　　　　Page 4 of 9

DATED : September 5, 1995

INVENTOR(S) : BRETTING

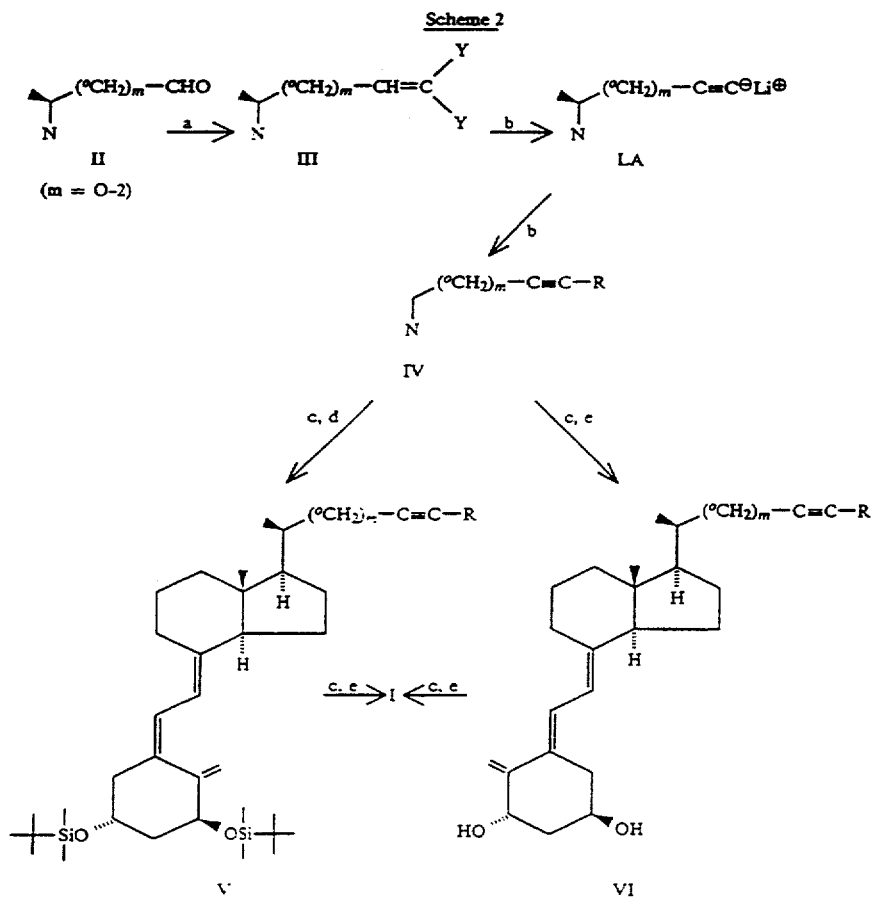

Notes to Scheme 2 a Reaction with a Wittig-type reagent, e.g. [(CH₃)₂N]₃P=CCl₂ or (C₆H₅)₃P=CBr₂ (see for example Salmond, W.G. et al., Tetrahedron Letters, 1977, 1141; (Y = Cl, resp. Br), in a suitable anhydrous solvent (e.g. dichloromethane).

b Treatment of III with two moles of a base, e.g. BuLi to give the intermediate lithium acetylide, LA, followed by alkylation with the side chain building block R-Z with or without catalyst (e.g. HMPA) in an anhydrous solvent (e.g. THF).

c Optional functional group modification in the side chain.

d Isomerisation with hν-triplet sensitizer, e.g. anthracene.

e Deprotection with TBA⁺F⁻ or HF.

UNITED STATES PATENT AND TRADEMARK OFFICE
CERTIFICATE OF CORRECTION

PATENT NO.    : 5,447,924
DATED         : September 5, 1995
INVENTOR(S)   : BRETTING It is certified that error appears in the above-identified patent and that said Letters Patent is hereby corrected as shown below:

Column 11-12, change Scheme 5

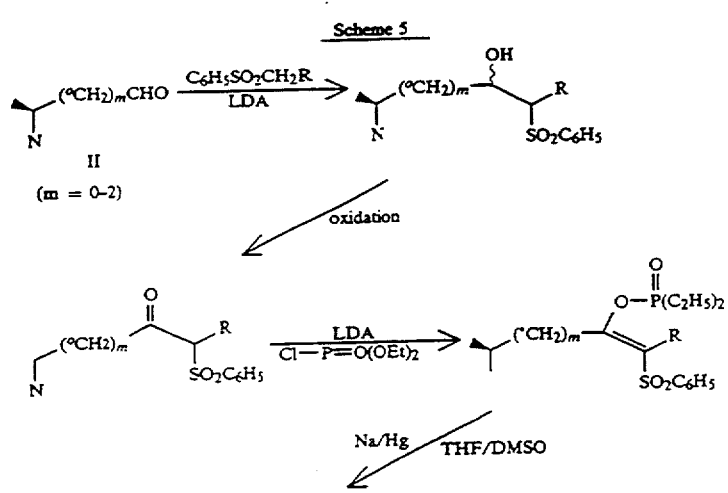

UNITED STATES PATENT AND TRADEMARK OFFICE
CERTIFICATE OF CORRECTION

PATENT NO. : 5,447,924   Page 6 of 9

DATED : September 5, 1995

INVENTOR(S) : BRETTING to --

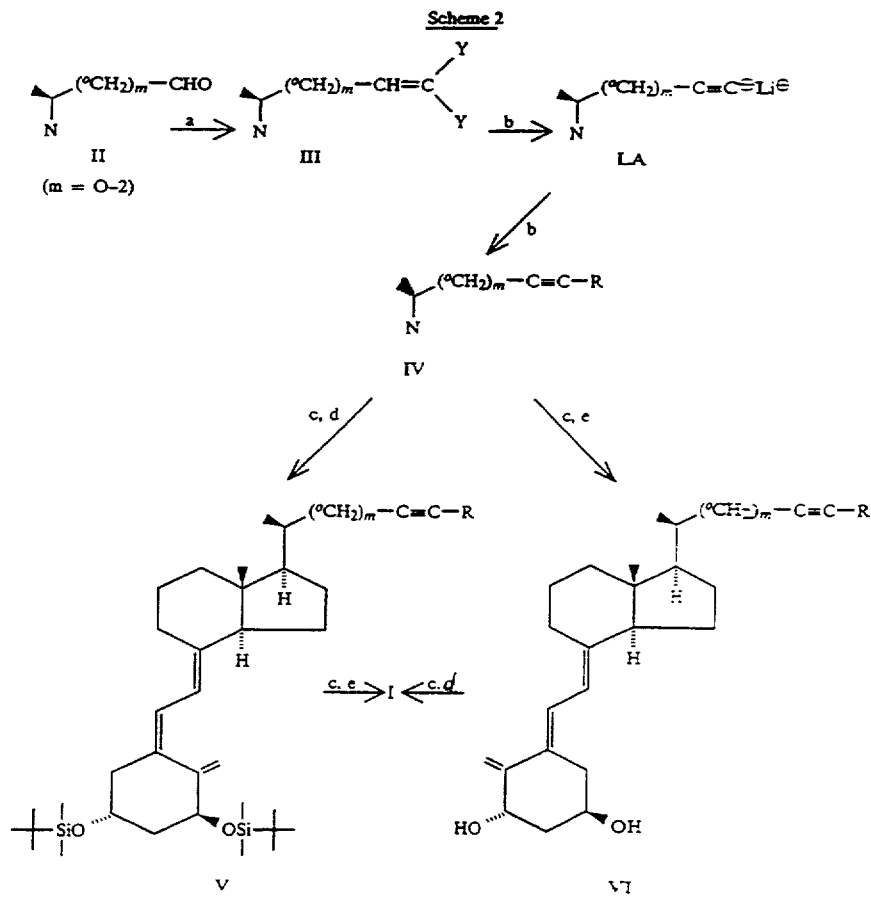

Notes to Scheme 2 a Reaction with a Wittig-type reagent, e.g. [(CH₃)₂N]₃P=CCl₂ or (C₆H₅)₃P=CBr₂ (see for example Salmond, W.G. et al., Tetrahedron Letters, 1977, 1141), (Y = Cl, resp. Br), in a suitable anhydrous solvent (e.g. dichloromethane).

b Treatment of III with two moles of a base, e.g. BuLi, to give the intermediate lithium acetylide, LA, followed by alkylation with the side chain building block R-Z with or without catalyst (e.g. HMPA) in an anhydrous solvent, e.g. THF.

c Optional functional group modification in the side chain.

d Isomerisation with hv-triplet sensitizer, e.g. anthracene.

e Deprotection with TBA⁺F⁻ or HF.

UNITED STATES PATENT AND TRADEMARK OFFICE
CERTIFICATE OF CORRECTION

PATENT NO. : 5,447,924 Page 7 of 9
DATED : September 5, 1995
INVENTOR(S) : BRETTING It is certified that error appears in the above-identified patent and that said Letters Patent is hereby corrected as shown below:

to --

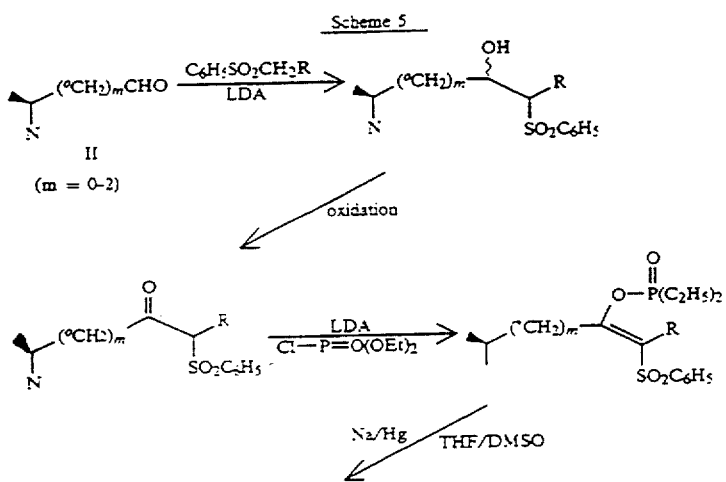

--

UNITED STATES PATENT AND TRADEMARK OFFICE
CERTIFICATE OF CORRECTION

PATENT NO.   :   5,447,924
DATED        :   September 5, 1995
INVENTOR(S)  :   BRETTING It is certified that error appears in the above-identified patent and that said Letters Patent is hereby corrected as shown below:

Column 13, line 28, insert --a) other leaving groups, e.g. triflate, may be introduced instead of tosylate--;

Column 14, line 46, change "Mount" to --amount--;

Column 18, line 13, change "(dd, 11{)" to --(dd, 1H)--;

Column 18, line 13, change "(m, 11{)" to --(m, 1 H)--;

Column 18, line 14, change "(m, 11{)" to --(m, 1 H)--;

Column 18, line 14, change "(d, 11{)" to --(d, 1 H)--;

UNITED STATES PATENT AND TRADEMARK OFFICE
CERTIFICATE OF CORRECTION

PATENT NO. : 5,447,924
DATED : September 5, 1995
INVENTOR(S) : BRETTING

It is certified that error appears in the above-indentified patent and that said Letters Patent is hereby corrected as shown below:

Column 21, line 50, change "-Dihydroxy-2.0(R)-" to -- -Dihydroxy-20(R)- --.

Signed and Sealed this

Ninth Day of July, 1996

Attest:

BRUCE LEHMAN

Attesting Officer     Commissioner of Patents and Trademarks